US 6,736,617 B2

(12) United States Patent
Domroese

(10) Patent No.: US 6,736,617 B2
(45) Date of Patent: May 18, 2004

(54) PERISTALTIC PUMP HAVING AUTOMATICALLY ADJUSTING BUSHING

(75) Inventor: Michael K. Domroese, Woodbury, MN (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 0 days.

(21) Appl. No.: 10/077,768

(22) Filed: Feb. 20, 2002

(65) Prior Publication Data

US 2003/0156957 A1 Aug. 21, 2003

(51) Int. Cl.$^7$ ................................................ F04B 43/12
(52) U.S. Cl. .................. 417/477.7; 417/477.8; 417/477.3
(58) Field of Search .................. 417/477.3, 477.7, 417/477.8

(56) References Cited

U.S. PATENT DOCUMENTS

| 3,116,697 A | | 1/1964 | Bilichniansky |
| 3,122,103 A | | 2/1964 | Ormsby |
| 3,137,242 A | | 6/1964 | Hahn |
| 3,700,361 A | | 10/1972 | De Vries |
| 3,737,256 A | | 6/1973 | De Vries |
| 3,762,836 A | | 10/1973 | De Vries |
| 4,043,712 A | | 8/1977 | Azzolini |
| 4,288,205 A | * | 9/1981 | Henk ........................ 417/477.3 |
| 4,524,861 A | * | 6/1985 | Matsushita ............. 198/781.04 |
| 4,548,553 A | * | 10/1985 | Ferster ...................... 417/477.7 |
| 4,558,996 A | * | 12/1985 | Becker ..................... 417/477.7 |
| 4,564,342 A | * | 1/1986 | Weber et al. ............. 417/477.7 |
| 4,720,249 A | * | 1/1988 | Krebs et al. .............. 417/477.8 |
| 4,832,585 A | | 5/1989 | Horiuchi |
| 5,062,775 A | | 11/1991 | Orth |
| 5,067,879 A | | 11/1991 | Carpenter |
| 5,110,270 A | * | 5/1992 | Morrick .................... 417/477.7 |
| 5,263,831 A | * | 11/1993 | Kappus .................... 417/477.7 |
| 5,499,907 A | | 3/1996 | Knott et al. |
| 5,657,000 A | * | 8/1997 | Ellingboe ................. 417/477.7 |
| 5,711,654 A | * | 1/1998 | Afflerbaugh ............. 417/477.2 |
| 5,759,017 A | * | 6/1998 | Patton et al. ............. 417/477.7 |
| 6,030,190 A | * | 2/2000 | Kammerer ................ 417/477.7 |

* cited by examiner

Primary Examiner—Cheryl J. Tyler
(74) Attorney, Agent, or Firm—Burns, Doane, Swecker & Mathis, LLP

(57) ABSTRACT

A roller pump includes a stator, a rotor assembly including a rotor hub, a first roller slide and a second roller slide slidingly disposed within the rotor hub, with each of the roller slides supporting a roller. At least one adjustable bushing is mounted within at least one of the roller slides. The roller slide includes a recess and the at least one adjustable bushing is at least partially disposed within the recess. The at least one adjustable bushing includes a bushing member and a spring member, the bushing member and the spring member being disposed within the recess in the roller slide.

15 Claims, 3 Drawing Sheets

PERISTALTIC PUMP HAVING AUTOMATICALLY ADJUSTING BUSHING

TECHNICAL FIELD

The present invention relates to a peristaltic pump for fluid transfer, such as blood circulation, dialytic fluid circulation or fluid medicine injection, and more particularly, to an adjustable occlusion peristaltic pump having an automatically adjusting bushing.

BACKGROUND OF THE INVENTION

Peristaltic pumps are commonly utilized in medical applications. For instance, such pumps are often employed during cardiovascular surgery to facilitate circulation of blood between a patient and a heart-lung machine. Other common medical uses are the transfer of blood between a patient and a kidney dialyzer, and intravenous feeding of IV solutions. Generally, peristaltic pumps are simply structured, generate a constant flow, and employ disposable tubes as a member for fluid transfer.

Peristaltic pumps are relatively simple in construction and typically include a housing having rollers which progressively compress a flexible tube at spaced intervals against an arcuate surface or raceway so as to flatten or locally reduce the cross-sectional area of the tube. In this manner, fluid leading to the flexible tube is continuously forced through the flexible tube by one or another of the rollers as it proceeds along the flexible tube over the arcuate surface or raceway.

A conventional roller pump 10, as shown in FIG. 1, comprises a drive mechanism 14 furnished with a drive shaft 12, a rotating shaft 16 which rotates according to the rotation of drive shaft 12, and a hollow pump head 20 fixed to a housing 18 to which drive mechanism 14 is attached. This pump head 20 integrally incorporates a bearing block 24 through which rotating shaft 16 is inserted and rotatably supported by a pair of bearings 22 and a stator 26 arranged on the upper portion of bearing block 24. On the upper surface of stator 26 is formed a recess 28 through which the upper end of rotating shaft 16 is protruded. While this recess 28 is radially and outwardly spaced at a certain distance from the outer circumferential surface of rotating shaft 16, its inner circumferential surface 28a is coaxial with rotating shaft 16.

A rotor assembly 30 is attached to the upper portion of rotating shaft 16 in such a way as to be placed inside recess 28 of stator 26 and to stay opposite the inner circumferential surface 28a thereof. This rotor 30 is fixed to rotating shaft 16 through a bolt 32, and is so constructed as to integrally rotate along with rotating shaft 16. On the outer circumferential surface of rotor 30, at least one roller 34 is arranged so as to rotate about its own axes. A tube 36 which is filled with blood or other fluid material is placed between rotor 30 and stator 26. Tube 36 is clamped between respective rollers 34, which are attached to rotor 30, and inner circumferential surface 28a of stator 26, thereby maintaining tube 36 in a closed state at the point at which it is clamped.

Thus, in a conventional roller pump 10, rotor 30 is rotated by the rotational motion of rotating shaft 16 driven by drive mechanism 14, and the clamped portions of tube 36 move according to the revolution of rollers 34 around rotating shaft 16. Therefore, fluid inside tube 36 is transferred according to the revolution of rollers 34. The rate of rotation of the rotating shaft 16 and hence the rollers 34 is normally adjustable so that the pumping rate of the fluid within tube 36 can be adjusted. However, the pumping rate can also be adjusted by adjusting the degree to which the rollers compress the flexible tube. This can be done in peristaltic pump assemblies by providing an adjustment mechanism for adjusting the distance between the axes of the rollers and hence the distance between the roller surface and the inner circumferential surface 28a of stator 26. Another important reason for peristaltic pumps to be adjustable in this fashion is that the compressibility, size, and other qualities of the flexible tube can vary considerably.

A rotor assembly 30' having an adjustable occlusion capability, as shown in FIG. 2, comprises a rotor hub 40, and opposing roller slides 42, each of which carries at least one roller 34 on the outer circumferential surface thereof. The roller slides 42 are extended or retracted from the hub 40 by turning the knob 44 on the top of the rotor hub. The extension or retraction of the roller slides thereby changes the occlusion of the flexible tube within the peristaltic pump. The roller slides 42 should be held securely to avoid knocking of the slides on the side, top, or bottom surfaces of the slot in the hub 40, particularly as the rollers 34 roll onto or off of the flexible tube in the pump. Because the flexible tube in a peristaltic pump is typically located in an approximately 180° arc around the rotating rotor, each roller 34 rolls onto and then off of the flexible tube once during each revolution of the rotor. Any knocking of the roller slides against the walls of the rotor hub produces a noise which has been found unacceptable in a surgical environment.

The roller slides in a peristaltic roller pump must therefore be held securely in order to avoid the unacceptable noise of the roller slide knocking against the hub. In order to prevent this knocking noise, the gap between the roller slide and the hub surface must be within approximately 0.001 inch on both the sides and the top and bottom of the slide. It is difficult and expensive to fabricate the hub and roller slides to maintain the gaps within this specification. The roller slides and hub are typically fabricated of aluminum and are anodized after machining. Considering the variation in geometry introduced by the anodization process, the height and width of the roller slides and hub must be machined to tolerances of approximately +/−0.0001 inch in order to obtain a 0.001 inch or less gap between the roller slides and hub. It is not practical to machine the parts to these tolerances. For the various occlusion mechanisms on the market, the most common approach used to obtain the 0.001 inch or less gap between the roller slides and hub relies on part size classification and custom fitting of parts. As a result, the roller slides in one pump do not necessarily fit properly in the hub of another pump, and hence classification and custom fitting of parts does not allow for easy service or replacement of the roller slides.

Accordingly, there is a need in the art for an improved system for mounting the roller slides in the hub of a rotor assembly which substantially eliminates the potential for knocking noises and significantly relaxes the machining tolerances for the roller slides and hub.

SUMMARY OF THE INVENTION

The present invention overcomes the disadvantages of the prior art by providing an adjustable bushing for use in a roller pump. The adjustable bushing comprises a preferably wedge shaped bushing member and a spring. The spring biases the wedge shaped bushing member in a recess in a portion of the roller pump; thereby compensating for any gap or spacing between the roller slide and the hub.

More particularly, the present invention is directed to a roller pump comprising a stator, a rotor assembly including a rotor hub, a first roller slide and a second roller slide slidingly disposed within the rotor hub, and each of the roller slides supporting a roller. At least one adjustable bushing is mounted within at least one of the roller slides to compensate for any gap or spacing between the roller slide and the hub. In a preferred embodiment, at least one of the roller slides includes a recess and the at least one adjustable bushing is at least partially disposed within the recess. The at least one adjustable bushing preferably comprises a bushing member and a spring member, the spring member biasing the bushing member within the recess. More preferably, the bushing member has a wedge shaped configuration and the recess is correspondingly tapered within a surface of one of the roller slides.

In a preferred embodiment of the present invention, the at least one adjustable bushing comprises a first adjustable bushing disposed within a side surface of at least one roller slide and a second adjustable bushing disposed within one of a top and a bottom surface of at least one roller slide.

The present invention is also directed to a rotor assembly for a peristaltic pump comprising a rotor hub, at least one roller slide slidingly disposed within the rotor hub, a roller supported by the at least one roller slide, and at least one adjustable bushing mounted within the at least one roller slide. The at least one roller slide preferably includes a recess and the at least one adjustable bushing is at least partially disposed within the recess. More preferably, the at least one adjustable bushing comprises a bushing member and a spring member, the spring member biasing the bushing member within the recess

BRIEF DESCRIPTION OF THE DRAWINGS

These, and other, objects, features and advantages of the present invention will become more readily apparent to those skilled in the art upon reading the following detailed description, in conjunction with the appended drawings, in which.

DETAILED DESCRIPTION OF THE PRESENT INVENTION

Figure 1:
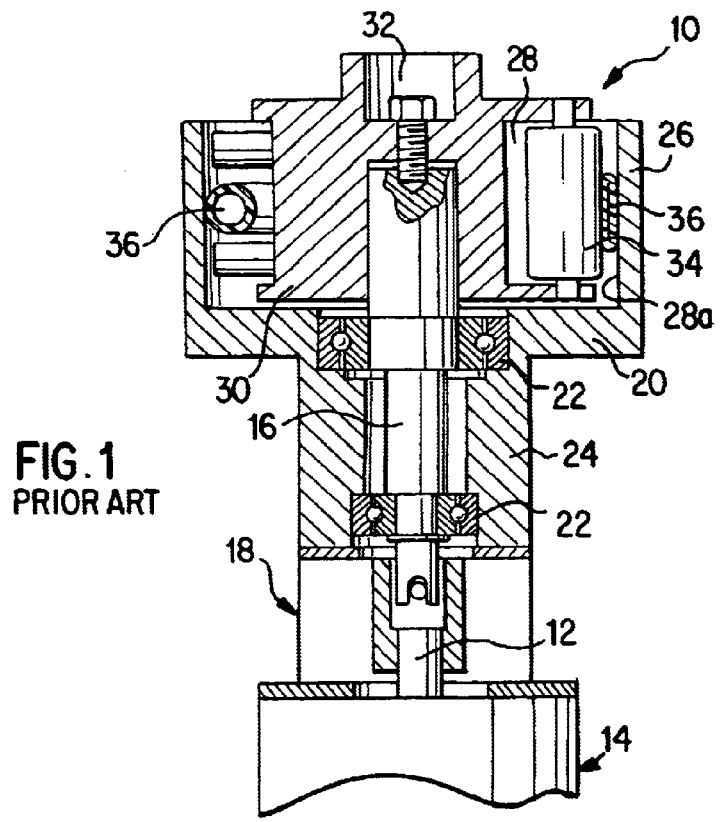
FIG. 1 is a cross-sectional view of a peristaltic pump as known in the prior art.
Figure 2:
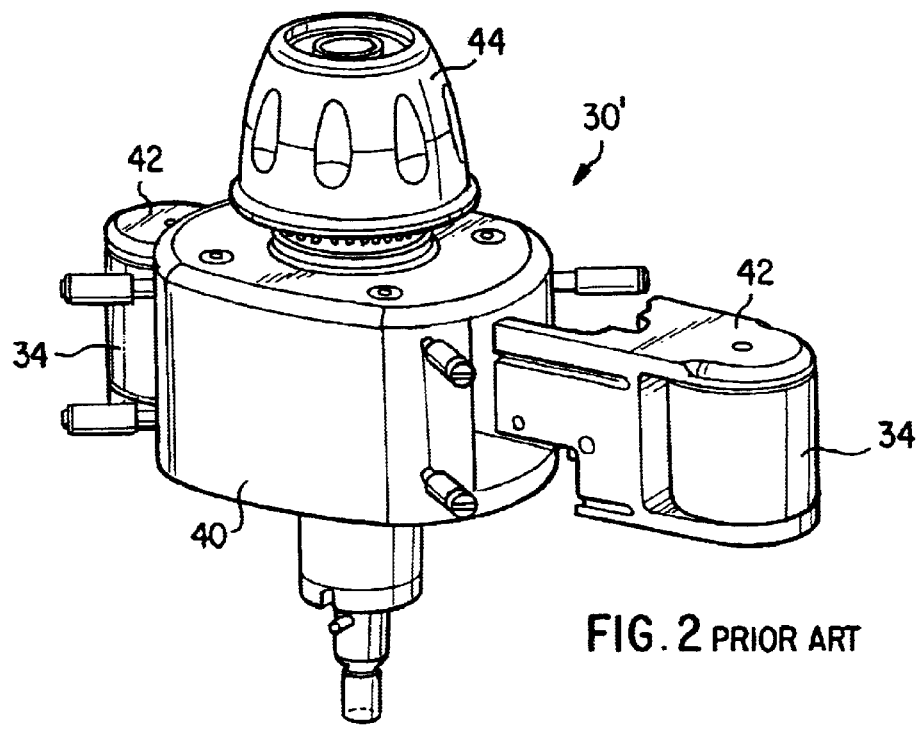
FIG. 2 is a perspective view of an alternative rotor assembly for a peristaltic pump as known in the art with one roller slide spaced radially outward for clarity.
Figure 3:
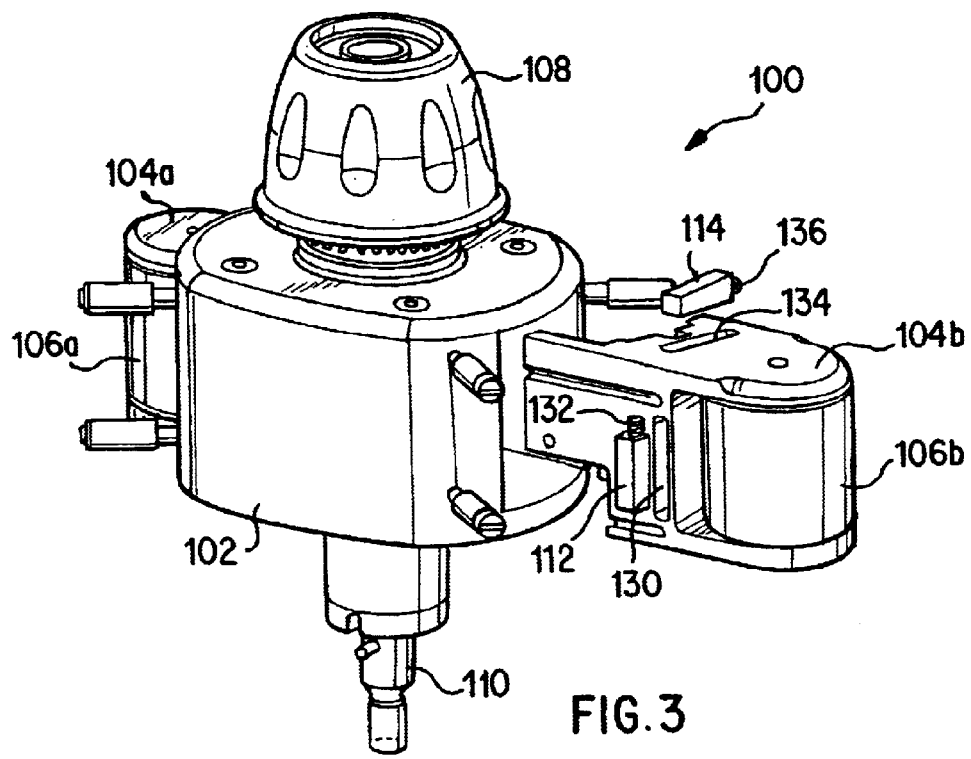
FIG. 3 is a perspective view of a rotor assembly for a peristaltic pump according to the present invention.

A peristaltic pump rotor assembly according to the present invention is shown generally by reference numeral 100 in FIG. 3. Rotor assembly 100 includes a pump or rotor hub 102, at least one and preferably two opposing roller slides 104a, 104b, a roller 106a, 106b disposed within each roller slide, respectively, and an adjustment knob 108 for adjusting the occlusion of the flexible tube within the pump. The rotor assembly 100 is rotatably supported within a stator similar to that shown in FIG. 1 and as known in the art, and the inner circumferential surface of the stator forms the raceway for the rollers 106a, 106b of the present invention. A main shaft 110 extending through the rotor assembly 100 rotates according to the rotation of a drive shaft, which is rotated by a conventional drive mechanism, as shown in FIG. 1, for example.

Figure 5:
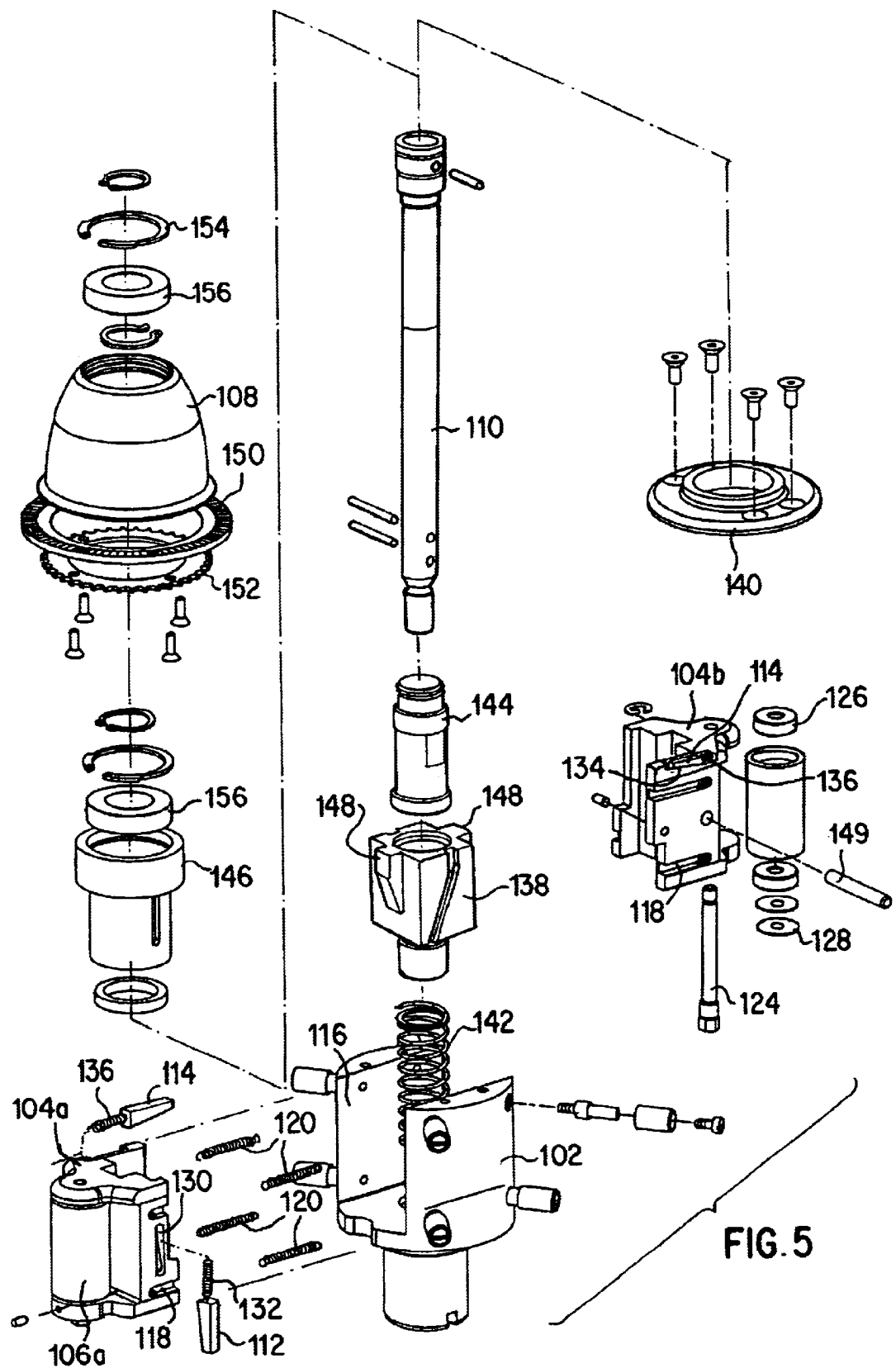
FIG. 5 is an exploded view thereof.

Referring also to FIG. 5, an exploded view of the rotor assembly 100 is illustrated. Each of the roller slides 104a, 104b preferably includes a plurality of recesses or channels 118 for receiving an extension spring 120. Each of the channels 118 includes, preferably at an outer end thereof, a peg to which the opposing ends of the springs are attached. As such, the opposing roller slides 104a and 104b are interconnected by a plurality of springs 120. The rollers 106a, 106b are firmly held in the proper position within the roller slides 104a, 104b, respectively, by a roller shaft 124. Various bearings 126 and washers 128 may also be used for mounting the rollers 106a, 106b within the roller slides 104a, 104b, respectively.

As shown in the illustrated embodiment, the rotor assembly 100 further includes a cam block 138 which is preferably spring loaded by a spring 142. A guide collar 144 engages an upper surface of the cam block 138 and vertically adjusts the position of cam block 138 through rotation of the adjustment knob 108 and a screw adjustment member 146 which moves downward and thereby correspondingly moves the guide collar 144 in a downward direction. The cam block 138 includes opposing wedge-shaped projections 148 which engage a corresponding dowel pin 149 on an inner surface of each roller slide 104a, 104b. Thus, as the adjustment knob 108 is rotated clockwise, for example, and screw adjustment member 146 correspondingly moves downward so as to move guide collar 144 in a downward direction, cam block 138 is also moved downward such that the wedge projections 148 on the cam block 138 force the roller slides 104a, 104b radially outward against the force of extension springs 120.

The adjustment knob 108 also includes an occlusion indicator ring 150 and a detent ring 152 for providing an audible indication of the degree of rotation of the knob 108. A plurality of retaining rings 154 and bearings 156 may also be provided.

Whereas the prior art categorized the sizes of the roller slides and the hub and hand-finished the same in order to achieve a tight fit therebetween, the present invention provides at least one, and preferably two, adjustable bushings or gibs 112, 114 to effectively compensate for any spacing or gaps that may be present between each roller slide 104a, 104b and an interior surface 116 of the pump hub 102. In a preferred embodiment of the invention, adjustable bushing 112 is provided on a side surface of each roller slide 104a and 104b in order to prevent any sideways motion caused by a horizontal gap within the pump hub 102. A further adjustable bushing 114 is preferably provided on a top and/or bottom surface of each of the roller slides 104a and 104b in order to similarly prevent any up and down motion of the roller slides 104a and 104b that may be caused by a vertical gap within the pump hub 102.

Each of the roller slides may further include an angled or sloped recess 130 in a side surface thereof. The recess 130 preferably receives the adjustable bushing 112 and a spring 132 which biases the horizontal gap bushing 112 firmly against a wall surface 116 of the pump hub. Similarly, a top and/or bottom surface of each of the roller slides 104a, 104b may include a second angled or sloped recess 134 for receiving the adjustable bushing 114 and a spring 136 which biases the vertical gap bushing 114 against a top or bottom surface of the pump hub. The second angled recess 134 for receiving the adjustable bushing 114 may be disposed in a side edge of the roller slide as shown in FIG. 5, or alternatively, the second angled recess 134 may be provided in a central area of the roller slide on a top or bottom surface thereof, as shown for example in FIG. 3. Other locations for the vertical gap adjustable bushing 114, as well as the horizontal gap adjustable bushings 112, would of course also be possible within the scope of the present invention so long as the bushings are situated between the roller slides and the inner surface of the hub.

Figure 4:
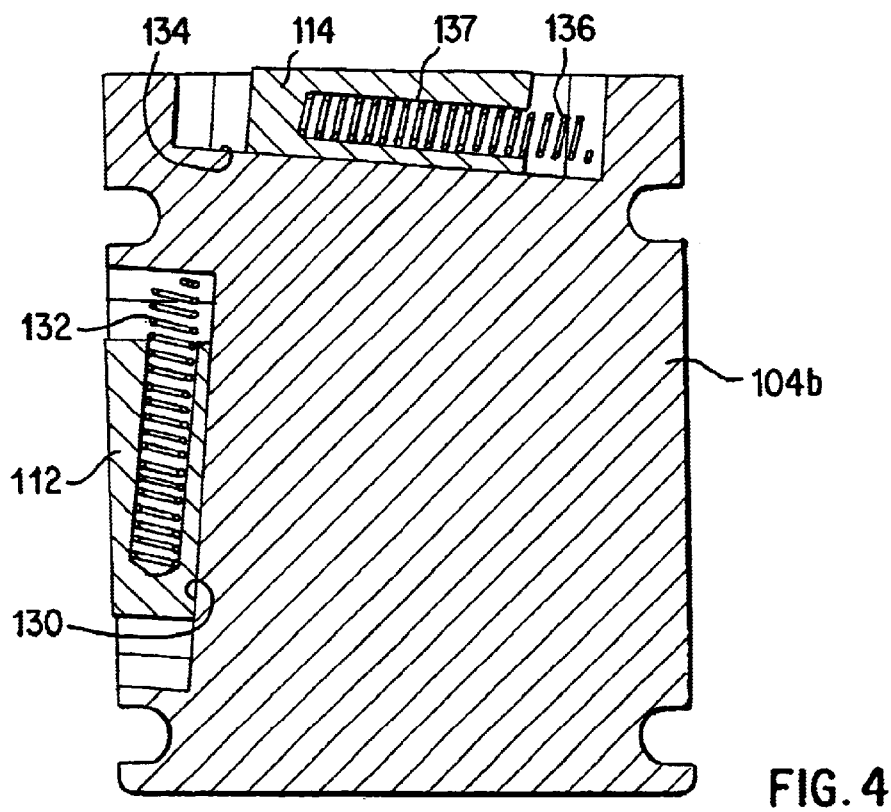
FIG. 4 is a cross section of the roller slide shown in FIG. 3.

Referring to FIG. 4, an enlarged cross-sectional view of the roller slide of FIG. 3 more clearly illustrates the preferred shape and configuration of the adjustable bushings 112, 114 and the angled recesses 130, 134 in which they are disposed. As illustrated in detail, the adjustable bushing 112 is mounted in a first angled recess 130 in a side of the roller slide to fill a horizontal gap between the roller slide and the hub slot. In a similar manner, the adjustable bushing 114 can be mounted in a second angled recess 134 in either the top or bottom of the roller slide in order to fill a vertical gap between the roller slide and the hub slot. The springs 132, 136, respectively, push the bushings 112, 114 into place, thereby filling the gaps between the roller slide and the interior surfaces of the hub.

The preferred rotor assembly of the present invention has a zero backlash mechanism such that the occlusion of the flexible tube in the pump may be either increased or decreased without creating any backlash, at least when the rotor assembly is clean and not contaminated with blood. Accordingly, the method used to mount the roller slides in the rotor hub should preferably not create any significant friction between the roller slides and the hub, otherwise the zero backlash feature of the mechanism may be compromised.

In order to fulfill this objective, the bushing itself is preferably given a small angle, resulting in the illustrated wedge-shaped configuration of FIG. 4. The bushings 112, 114 rather than the springs 132, 136 thus bear most of the force from the roller slide as the roller rolls against the tube and the pump. The springs for pushing the respective bushings into place can therefore be very light, such that the bushings do not significantly increase the friction between the roller slides and the hub as the pump occlusion is adjusted, and the backlash feature of the pump is not adversely influenced.

In the exemplary illustrated embodiment, the first and second angled recesses 130, 134 have a length of approximately 0.690", a first depth of approximately 0.120" and a second depth of approximately 0.680" so as to define an approximately 10° angle. Each of the bushings 112, 114 has a length of approximately 0.462", a first depth of approximately 0.140" and a second depth of approximately 0.440", so as to also define an angle of approximately 10°. Each of the bushings may further include a spring receiving slot 137 for receiving one end of a spring 132, 136. In a preferred embodiment, bushings 112, 114 are made of Delrin®, or an acetal resin material. The springs 132, 136 are preferably stainless steel springs having an approximately 0.120" outer diameter and which are approximately 0.44" long with a spring constant of approximately 2.9 lb/in. The preferred springs 132, 136 were found to push the bushings 112, 114 into place in the exemplary embodiment with a nominal force of 0.1 lbs. With the bushings installed in a prototype device, no detectable noise occurred as the pump was run at speeds from 0 to 250 rpm and at various levels of tube occlusion. The above-described dimensions are specific with respect to the disclosed embodiment of the present invention; it should be clear to one skilled in the art, however, that other dimensions and sizes could also be utilized within the scope of the present invention depending upon the size and configuration of the desired installation.

In order to install the adjustable bushings of the present invention in the rotor assembly 100, the following preferred procedure is followed. The horizontal gap or side bushings 112 are first loaded into the first angled recesses 130 and the spring 132 is loaded therein. The roller slides 104a, 104b are then disposed within the pump hub 102. At this point, the vertical gap or top bushings 114 are loaded into their respective second angled recesses 134 and the springs 136 are similarly disposed within the recess. A cover 140 is then installed on the pump hub 102 so as to hold the top bushings 114 and the remaining inner workings of the rotor assembly in place.

The present invention provides adjustable bushings for mounting the roller slides of a pump hub of a rotor assembly which eliminates the potential for knocking noises while significantly relaxing the machining tolerances for the roller slides and the hub. The present invention thus significantly reduces the cost and time required to manufacture both the slides and hub. In a preferred embodiment of the present invention, machining tolerances for the height and width of the roller slides and the pump hub slot can be on the order of +/−0.002 inches or perhaps even up to +/−0.005 inches (rather than the +/−0.0001 inch required by the prior art) since the automatically adjusting bushings will fill gaps of up to at least 0.015 inch. In addition, no custom fitting of the roller slides to the hub is required. The automatically adjusting bushings of the present invention thus makes it feasible and easy to service and replace the roller slides in a peristaltic pump.

While the present invention has been described with preferred embodiments, it is to be understood that variations and modifications may be resorted to as will be apparent to those skilled in the art. Such variations and modifications are to be considered within the purview and the scope of the present invention.

What is claimed is:

1. A roller pump comprising:
   a stator;
   a rotor assembly including a rotor hub, a first roller slide and a second roller slide slidingly disposed within said rotor hub, each of said roller slides supporting a roller;
   means for driving the rotor assembly;
   an occlusion adjustment mechanism slidingly adjusting a radial position of said roller slides relative to said rotor hub; and
   at least one adjustable bushing mounted between said rotor hub and at least one of said roller slides, said at least one adjustable bushing compensating for gaps between an inner surface of said rotor hub and said roller slide so as to reduce movement of said roller slide relative to said rotor hub in at least one of a horizontal and vertical direction.

2. The roller pump of claim 1 wherein said at least one of said roller slides includes a recess and said at least one adjustable bushing is at least partially disposed within said recess.

3. The roller pump of claim 2 wherein said at least one adjustable bushing comprises a bushing member and a spring member, said spring member biasing said bushing member within said recess.

4. The roller pump of claim 3 wherein said bushing member has a wedge shaped configuration.

5. The roller pump of claim 3 wherein said bushing member includes an internal recess for receiving at least a portion of said spring member.

6. The roller pump of claim 2 wherein said recess is tapered within a surface of said at least one of said roller slides.

7. The roller pump of claim 1 wherein said at least one adjustable bushing comprises a first adjustable bushing disposed within a side surface of at least one roller slide and a second adjustable bushing disposed within one of a top and a bottom surface of at least one roller slide.

8. A rotor assembly for a peristaltic pump having a means for driving the rotor assembly, said rotor assembly comprising:

a rotor hub;

at least one roller slide slidingly disposed within said rotor hub, said at least one roller slide being radially positionable relative to said rotor hub, and;

a roller supported by said at least one roller slide;

at least one adjustable bushing mounted within said at least one roller slide, said at least one adjustable bushing compensating for gaps between an inner surface of said rotor hub and said roller slide so as to reduce movement of said roller side relative to said rotor hub in at least one of a horizontal and vertical direction.

9. The rotor assembly of claim 8 wherein said at least one roller slide includes a recess and said at least one adjustable bushing is at least partially disposed within said recess.

10. The rotor assembly of claim 9 wherein said at least one adjustable bushing comprises a bushing member and a spring member, said bushing member and said spring member being disposed within said recess.

11. The rotor assembly of claim 10 wherein said bushing member has a wedge shaped configuration.

12. The rotor assembly of claim 9 wherein said recess is tapered within a surface of said at least one roller slide.

13. The rotor assembly of claim 8 wherein said at least one adjustable bushing comprises a first adjustable bushing disposed within a side surface of said at least one roller slide and a second adjustable bushing disposed within one of a top and a bottom surface of said at least one roller slide.

14. An adjustable bushing for use in a rotor assembly including a roller slide and a hub, said adjustable bushing comprising:

a bushing member; and a spring for biasing said bushing member between the roller slide and the hub, thereby compensating for any gap between the roller slide and the hub;

wherein said bushing member is wedge shaped.

15. A roller pump comprising:

a stator;

a rotor assembly including a rotor hub, a first roller slide and a second roller slide slidingly disposed within said rotor hub, each of said roller slides supporting a roller;

means for driving the rotor assembly; and at least one adjustable bushing mounted between said rotor hub and at least one of said roller slides;

wherein said at least one adjustable bushing comprises a first adjustable bushing disposed within a side surface of at least one roller slide and a second adjustable bushing disposed within one of a top and a bottom surface of at least one roller slide.

* * * * *